(12) United States Patent
Ray, II

(10) Patent No.: US 9,999,604 B2
(45) Date of Patent: Jun. 19, 2018

(54) COMPOUNDED SOLUTIONS OF DICLOFENAC AND LIDOCAINE AND METHODS

(71) Applicant: CMPD LICENSING, LLC, Conroe, TX (US)

(72) Inventor: Jay Richard Ray, II, Conroe, TX (US)

(73) Assignee: CMPD LICENSING, LLC, Conroe, TX (US)

(*) Notice: Subject to any disclaimer, the term of this patent is extended or adjusted under 35 U.S.C. 154(b) by 0 days. days.

(21) Appl. No.: 15/354,630

(22) Filed: Nov. 17, 2016

(65) Prior Publication Data

US 2018/0133178 A1    May 17, 2018

(51) Int. Cl.
| A61K 31/196 | (2006.01) |
| A61K 31/167 | (2006.01) |
| A61K 47/20 | (2006.01) |
| A61K 9/00 | (2006.01) |

(52) U.S. Cl.
CPC .......... *A61K 31/196* (2013.01); *A61K 9/0014* (2013.01); *A61K 31/167* (2013.01); *A61K 47/20* (2013.01)

(58) Field of Classification Search
CPC ... A61K 9/0014; A61K 31/196; A61K 31/167
See application file for complete search history.

(56) References Cited

U.S. PATENT DOCUMENTS

| 4,711,906 | A | * | 12/1987 | von Stetten .......... A61K 9/0019 514/538 |
| 5,407,663 | A |  | 4/1995 | Eisen |
| 5,524,622 | A |  | 6/1996 | Wilson |
| 5,603,943 | A |  | 2/1997 | Yanagawa |
| 5,668,119 | A |  | 9/1997 | Medencia |
| 6,066,629 | A |  | 5/2000 | Moir et al. |
| 6,093,417 | A |  | 7/2000 | Petrus |
| 6,299,608 | B1 |  | 10/2001 | Solomon et al. |
| 8,084,445 | B2 |  | 12/2011 | Huq et al. |
| 8,129,364 | B2 |  | 3/2012 | Chaudry |
| 8,318,817 | B2 |  | 11/2012 | Lichter et al. |
| 8,338,648 | B2 |  | 12/2012 | Stock et al. |
| 8,663,663 | B1 |  | 3/2014 | Ray |
| 9,078,853 | B2 |  | 7/2015 | Ray |
| 2002/0061281 | A1 |  | 5/2002 | Osbakken |
| 2003/0143162 | A1 |  | 7/2003 | Speirs et al. |
| 2004/0235807 | A1 |  | 11/2004 | Weinrich et al. |
| 2005/0004002 | A1 |  | 1/2005 | Desai et al. |
| 2005/0053563 | A1 |  | 3/2005 | Manissier et al. |
| 2005/0148570 | A1 |  | 7/2005 | Huang et al. |
| 2006/0157507 | A1 |  | 7/2006 | Chang et al. |
| 2006/0228306 | A1 |  | 10/2006 | Lane |
| 2007/0037776 | A1 |  | 2/2007 | Richardson et al. |
| 2007/0065373 | A1 |  | 3/2007 | Morton et al. |
| 2007/0231274 | A1 |  | 10/2007 | Bhasin |
| 2007/0293460 | A1 |  | 12/2007 | Ray et al. |
| 2010/0183625 | A1 |  | 7/2010 | Sternlicht |
| 2011/0081411 | A1 |  | 4/2011 | Perrett et al. |
| 2011/0160118 | A1 |  | 6/2011 | Podolsky |
| 2011/0224176 | A1 |  | 9/2011 | Dobak et al. |
| 2012/0132204 | A1 |  | 5/2012 | Lucking et al. |
| 2012/0164080 | A1 |  | 6/2012 | Hill et al. |
| 2012/0213869 | A1 | * | 8/2012 | Ma .................... A61K 31/165 424/727 |
| 2012/0328671 | A1 |  | 12/2012 | O'Neil et al. |
| 2013/0149345 | A1 |  | 6/2013 | Lipp et al. |
| 2013/0165429 | A1 | * | 6/2013 | Ray, II ............... A61K 31/5415 514/226.5 |
| 2014/0371134 | A1 |  | 12/2014 | Ray |
| 2014/0371179 | A1 |  | 12/2014 | Simmons |
| 2015/0141515 | A1 | * | 5/2015 | Stoltenberg ............ A61K 47/32 514/567 |
| 2015/0313836 | A1 |  | 11/2015 | Ray |
| 2016/0166505 | A1 |  | 6/2016 | Ray |

FOREIGN PATENT DOCUMENTS

| JP | 10-109928 | 4/1998 |
| WO | 2006060027 | 6/2006 |
| WO | 2010109434 | 9/2010 |

OTHER PUBLICATIONS

Kanai et al., "Efficacy of a Metered-dose 8% Lidocaine Pump Spray for Patients with Post-herpetic Neuralgia," Pain Med. 10(5), 902-09 (2009).*
"4% Xylocaine®-MPF (lidocaine HCl) Sterile Solution" prescribing information, APP Pharmaceuticals, LLC (Feb. 2010).*
Sankar et al., "Local drug delivery for oral mucosal diseases: challenges and opportunities," Oral Diseases, 2011, vol. 17, Supplement 1, pp. 73-84.
Solares et al., "Treatment of chronic rhinosinusitis exacerbations due to methicillin-resistant *Staphylococcus aureus* with mupirocin irrigations," American Journal of Otolaryngology—Head and Neck Medicine and Surgery, 2006, vol. 27, pp. 161-165.
Uren et al., Nasal Lavage With Mupirocin For The Treatment of Surgically Recalcitrant Chronic Rhinosinusitis, Laryngocope, 2008, vol. 118, pp. 1677-1680.
Arora et al., (2011) Voriconazole versus natamycin as primary treatment in fungal corneal ulcers. Clin Experiment Ophthalmol. 39(5):434-440.
Aykut et al., (2010) Mupirocin application at the exit site in peritoneal dialysis patients: five years of experience. Ren Fail. 32(3):356-361. (Abstract Only).
Bai et al., (2010) Short-term comparative study of the effects of preserved and unpreserved topical levofloxacin on the human ocular surface. Cutan Ocul Toxicol. 29(4):247-253. (Abstract Only).
Barikbin et al., (2009) Pimecrolimus 1% cream versus betamethasone 17-valerate 0.1% cream in the treatment of facial discoid lupus erythematosus: a double-blind, randomized pilot study. Clin Exp Dermatol. 34(7):776-780. (Abstract Only).

(Continued)

*Primary Examiner* — Theodore R. West
(74) *Attorney, Agent, or Firm* — Akerman LLP

(57) ABSTRACT

A compounded topical solution may include approximately 85% to approximately 95% (v/v) diclofenac sodium topical solution, 1.5% (w/w), and approximately 5% to approximately 15% (v/v) lidocaine hydrochloride topical solution, 4% USP.

7 Claims, 4 Drawing Sheets

(56) References Cited

OTHER PUBLICATIONS

Barker et al., (1995) Oral care with vancomycin paste for reduction in incidence of alpha-hemolytic streptococcal sepsis. J Pediatr Hematol Oncol. 17(2):151-155. (Abstract Only).
Bassiri-Jahromi et al., (2012) A comparative evaluation of combination therapy of fluconazole 1% and urea 40% compared with fluconazole 1% alone in a nail lacquer for treatment of onychomycosis: therapeutic trial. J Dermatolog Treat. 23(6):453-456. (Abstract Only).
Bleecker et al., (2012) Once-daily fluticasone furoate is efficacious in patients with symptomatic asthma on low-dose inhaled corticosteroids. Ann Allergy Asthma Immunol. 109(5):353-358. (Abstract Only).
Cagle et al., (1981-1982) Topical tobramycin and gentamicin sulfate in the treatment of ocular infections: multicenter study. Curr Eye Res. 1(9):523-534. (Abstract Only).
Camacho et al., (2002) Oral and topical L-phenylalanine, clobetasol propionate, and UVA/sunlight—a new study for the treatment of vitiligo. J Drugs Dermatol. 1(2):127-131. (Abstract Only).
Carr et al., (2012) Comparison of intranasal azelastine to intranasal fluticasone propionate for symptom control in moderate-to-severe seasonal allergic rhinitis. Allergy Asthma Proc. 33(6):450-458. (Abstract Only).
Chang et al., (2012) A randomized, double-blind, placebo-controlled, pilot study to assess the efficacy and safety of clindamycin 1.2% and tretinoin 0.025% combination gel for the treatment of acne rosacea over 12 weeks. J Drugs Dermatol. 11(3):333-339. (Abstract Only).
Cherian et al., (2013) Oral antibiotics versus topical decolonization to prevent surgical site infection after Mohs micrographic surgery—a randomized, controlled trial. Dermatol Surg. 39(10):1486-1493. (Abstract Only).
Chiambaretta et al., (2008) Tear concentrations of azithromycin following topical administration of a single dose of azithromycin 0.5%, 1.0%, and 1.5% eyedrops (T1225) in healthy volunteers. Eur J Ophthalmol. 18(1):13-20.
Clareus et al., (2009) The DESIRE study—psoriasis patients' satisfaction with topical treatment using a fixed combination of calcipotriol and betamethasone dipropionate in daily clinical practice. Eur J Dermatol. 19(6):581-585. (Abstract Only).
Colin et al., (2003) Corneal penetration of levofloxacin into the human aqueous humour: a comparison with ciprofloxacin. Acta Ophthalmol Scand. 81(6):611-613.
Comstock et al., (2012) Safety and tolerability of loteprednol etabonate 0.5% and tobramycin 0.3% ophthalmic suspension in pediatric subjects. Paediatr Drugs. 14(2):119-130.
Corradini et al., (2006) Amphotericin B and lysine acetylsalicylate in the combined treatment of nasal polyposis associated with mycotic infection. J Investig Allergol Clin Immunol. 16(3):188-193.
Dehghani et al., (2009) Cefazolin-Gentamicin versus Vancomycin-Ceftazidime Eye Drops for Bacterial Corneal Ulcers;a Randomized Clinical Trial. J Ophthalmic Vis Res. 4(1):19-23.
Denis et al., (2008) Microbiological efficacy of 3-day treatment with azithromycin 1.5% eye-drops for purulent bacterial conjunctivitis. Eur J Ophthalmol. 18(6):858-868.
Dransfield et al., (2013) Once-daily inhaled fluticasone furoate and vilanterol versus vilanterol only for prevention of exacerbations of COPD: two replicate double-blind, parallel-group, randomised controlled trials. Lancet Respir Med. 1(3):210-223. (Abstract Only).
Du Bois et al., (1999) Randomized trial of inhaled fluticasone propionate in chronic stable pulmonary sarcoidosis: a pilot study. Eur Respir J. 13(6):1345-1350. (Abstract Only).
Epstein et al., (2002) Fluconazole mouthrinses for oral candidiasis in postirradiation, transplant, and other patients. Oral Surg Oral Med Oral Pathol Oral Radiol Endod. 93(6):671-675. (Abstract Only).
Fadlallah et al., (2012) Azithromycin 1.5% ophthalmic solution: efficacy and treatment modalities in chronic blepharitis. Arq Bras Oftalmol. 75(3):178-182.

Feldman et al., (2009) Topical clobetasol propionate in the treatment of psoriasis: a review of newer formulations. Am J Clin Dermatol. 10(6):397-406.
Findlay et al., (2013) Increased peritoneal dialysis exit site infections using topical antiseptic polyhexamethylene biguanide compared to mupirocin: results of a safety interim analysis of an open-label prospective randomized study. Antimicrob Agents Chemother. 57(5):2026-2028.
drugbank.com, Fluticasone Propionate—Accession No. DB00588, (2015) Available at http://www.drugbank.ca/drugs/DB00588, document of 17 pages.
Flynn et al., (1995) Oropharyngeal candidiasis in immunocompromised children: a randomized, multicenter study of orally administered fluconazole suspension versus nystatin. The Multicenter Fluconazole Study Group. J Pediatr. 127(2):322-328. (Abstract Only).
Fowler et al., (2002) A randomized double-blind study to compare the effects of nasal fluticasone and betamethasone on the hypothalamo-pituitary-adrenal axis and bone turnover in patients with nasal polyposis. Clin Otolaryngol Allied Sci. 27(6):489-493. (Abstract Only).
Gallenga et al., (1999) Topical lomefloxacin 0.3% twice daily versus tobramycin 0.3% in acute bacterial conjunctivitis: A multicenter double-blind phase III study. Ophthalmologica. 213(4):250-257. (Abstract Only).
Giavina-Bianchi et al., (2008) Fluticasone furoate nasal spray in the treatment of allergic rhinitis. Ther Clin Risk Manag. 4(2):465-472.
Goldberg et al., (2002) The use of otic powder in the treatment of acute external otitis. Am J Otolaryngol. 23(3):142-147. (Abstract Only).
Grossman et al., (1993) Fluticasone propionate aqueous nasal spray is safe and effective for children with seasonal allergic rhinitis. Pediatrics. 92(4):594-599. (Abstract Only).
Grove et al., (2013) Tolerability and irritation potential of four topical acne regimens in healthy subjects. J Drugs Dermatol. 12(6):644-649. (Abstract Only).
Howland et al. (1996) The efficacy of fluticasone propionate aqueous nasal spray for allergic rhinitis and its Relationship to topical effects. Clin Ther. 18(6):1106-1117. (Abstract Only).
Howland, (1996) Fluticasone propionate: topical or systemic effects? Clin Exp Allergy. 26 Suppl 3:18-22. (Abstract Only).
Jarratt et al., (2012) Efficacy and safety of clindamycin-tretinoin gel versus clindamycin or tretinoin alone in acne vulgaris: a randomized, double-blind, vehicle-controlled study. J Drugs Dermatol. 11(3):318-326. (Abstract Only).
Keith, (2012) Fluticasone furoate nasal spray reduces symptoms of uncomplicated acute rhinosinusitis: a randomised placebo-controlled study. Prim Care Respir J. 21(3):267-275.
Khodaeiani et al., (2013) Topical 4% nicotinamide vs. 1% clindamycin in moderate inflammatory acne vulgaris. Int J Dermatol. 52(8):999-1004. (Abstract Only).
Laforce et al., (2013) Ocular safety of fluticasone furoate nasal spray in patients with perennial allergic rhinitis: a 2-year study. Ann Allergy Asthma Immunol. 111(1):45-50. (Abstract Only).
Lelitha et al., (2014) In vitro susceptibility of filamentous fungal isolates from a corneal ulcer clinical trial. Am J Ophthalmol. 157(2):318-326.
Mahdy et al., (2010) Topical amphotericin B and subconjunctival injection of fluconazole (combination therapy) versus topical amphotericin B (monotherapy) in treatment of keratomycosis. J Ocul Pharmacol Ther. 26(3):281-285. (Abstract Only).
Man et al., (2013) The effect of intranasal fluticasone propionate irrigations on salivary cortisol, intraocular pressure, and posterior subcapsular cataracts in postsurgical chronic rhinosinusitis patients. Int Forum Allergy Rhinol. 3(12):953-957. (Abstract Only).
Mchugh et al., (2004) A topical azithromycin preparation for the treatment of acne vulgaris and rosacea. J Dermatolog Treat. 15(5):295-302. (Abstract Only).
Meltzer, (1997) The pharmacological basis for the treatment of perennial allergic rhinitis and non-allergic rhinitis with topical corticosteroids. Allergy. 52(36 Suppl):33-40.

(56) References Cited

OTHER PUBLICATIONS

Milgrom et al., (2009) Xylitol pediatric topical oral syrup to prevent dental caries: a double-blind randomized clinical trial of efficacy. Arch Pediatr Adolesc Med. 163(7):601-607.
Mino De Kaspar et al., (2008) A prospective randomized study to determine the efficacy of preoperative topical levofloxacin in reducing conjunctival bacterial flora. Am J Ophthalmol. 145(1):136-142.
Miura et al., (2009) Topical clindamycin in post-adenotonsillectomy analgesia in children: a double-blind, randomized clinical trial. Otolaryngol Head Neck Surg. 141(4):509-515. (Abstract Only).
Predel et al. (2013) A randomized, double-blind, placebo-controlled multicentre study to evaluate the efficacy and safety of diclofenac 4% spray gel in the treatment of acute uncomplicated ankle sprain. J Int Med Res. 41(4):1187-1202.
Simon et al., (2009) Efficacy and safety of topical diclofenac containing dimethyl sulfoxide (DMSO) compared with those of topical placebo, DMSO vehicle and oral diclofenac for knee osteoarthritis. Pain. 143(3):238-245.
Moen, (2009) Topical diclofenac solution. Drugs. 69(18):2621-2632.
Peniston et al., (2012) Long-term tolerability of topical diclofenac sodium 1% gel for osteoarthritis in seniors and patients with comorbidities. Clin Interv Aging. 7:517-523.
Roth et al., (2011) Diclofenac sodium topical solution 1.5% w/w with dimethyl sulfoxide compared with placebo for the treatment of osteoarthritis: pooled safety results. Postgrad Med. Nov. 2011;123(6):180-8. (Abstract Only).
Taylor et al, (2011) Safety profile of topical diclofenac: a meta-analysis of blinded, randomized, controlled trials in musculoskeletal conditions. Cuff Med Res Opin. Mar. 2011;27(3):605-22. (Abstract Only).
Baraf et al., (2011) Safety and efficacy of topical diclofenac sodium gel for knee osteoarthritis in elderly and younger patients: pooled data from three randomized, double-blind, parallel-group, placebo-controlled, multicentre trials. Drugs Aging. Jan. 1, 2011;28(1):27-40. (Abstract Only).
Predel et al., (2013) Efficacy and safety of diclofenac diethylamine 1.16% gel in acute neck pain: a randomized, double-blind, placebo-controlled study. BMC Musculoskelet Disord. Aug. 21, 2013;14:250.
González De Vega et al., (2013) Traumeel vs. diclofenac for reducing pain and improving ankle mobility after acute ankle sprain: a multicentre, randomised, blinded, controlled and non-inferiority trial. Int J Clin Pract. Oct. 2013;67(10):979-89.
Ahmed et al., (2015) Effect of 1.5% Topical Diclofenac on Clinical Neuropathic Pain. Anesthesiology. Jul. 2015;123(1):191-8.
Derry et al, (2012) Topical NSAIDs for chronic musculoskeletal pain in adults. Cochrane Database Syst Rev. Sep. 12, 2012;(9):CD007400.
Derry et al., (2015) Topical NSAIDs for acute musculoskeletal pain in adults. Cochrane Database Syst Rev. Jun. 11, 2015;(6):CD007402.
Yan et al., (2014) Can diclofenac ester prodrug promote direct penetration across the skin? Journal of Chemical and Pharmaceutical Research, 6(7):2701-2713.
Singer et al., (2015) Topical NSAIDs effect on corneal sensitivity. Cornea. May 2015;34(5):541-3.
Wadsworth et al., (2016) Efficacy and safety of diclofenac sodium 2% topical solution for osteoarthritis of the knee: a randomized, double-blind, vehicle-controlled, 4 week study. Curr Med Res Opin. 2016;32(2):241-50.
Alañón et al., (2014) Comparison between topical anaesthesia with cocaine versus lidocaine plus adrenaline for outpatient laser dacryocystorhinostomy. Arch Soc Esp Oftalmol. 89(2):53-57.
Kwon et al., (2012) Treatment for postoperative wound pain in gynecologic laparoscopic surgery: topical lidocaine patches. J Laparoendosc Adv Surg Tech A. 22(7):668-673.
Christensen et al., (2013) Lidocaine analgesia for removal of wound vacuum-assisted closure dressings: a randomized double-blinded placebo-controlled trial. J Orthop Trauma. 27(2):107-112.
Lee et al., (2013) The effect of buffered lidocaine in local anesthesia: a prospective, randomized, double-blind study. J Hand Surg Am. 38(5):971-975.
Gaviola et al., (2013) A prospective, randomized, double-blind study comparing the efficacy of topical anesthetics in nasal endoscopy. Laryngoscope. 123(4):852-858.
Coudert et al., (2014) Phase III, randomized, double-blind, placebo-controlled trial of topical 2 % lidocaine for the prevention and treatment of oral mucosal pain in children. Clin Oral Investig. 18(4):1189-1194.
Nayak et al. (2006) Evaluation of three topical anaesthetic agents against pain: a clinical study. Indian J Dent Res. 17(4):155-160.
Wolff et al., (2011) 5% lidocaine-medicated plaster vs other relevant interventions and placebo for post-herpetic neuralgia (PHN): a systematic review. Acta Neural Scand. May 2011;123(5):295-309.
Nalamachu et al., (2006) A comparison of the lidocaine patch 5% vs naproxen 500 mg twice daily for the relief of pain associated with carpal tunnel syndrome: a 6-week, randomized, parallel-group study. MedGenMed. Aug. 9, 2006;8(3):33.
Ernst et al., (1995) Lidocaine adrenaline tetracaine gel versus tetracaine adrenaline cocaine gel for topical anesthesia in linear scalp and facial lacerations in children aged 5 to 17 years. Pediatrics. Feb. 1995;95(2):255-8. (Abstract Only).
Kanai et al., (2010) Lidocaine eye drops attenuate pain associated with ophthalmic postherpetic neuralgia. May 1, 2010;110(5):1457-60.
Zink et al., (2011) Lidocaine patches reduce pain in trauma patients with rib fractures. Am Surg. Apr. 2011;77(4):438-42. (Abstract Only).
Taddio et al., (2002) Lidocaine-prilocaine cream versus tetracaine gel for procedural pain in children. Ann Pharmacother. 36(4):687-692. (Abstract Only).
Ingalls et al., (2010) Randomized, double-blind, placebo-controlled trial using lidocaine patch 5% in traumatic rib fractures. J Am Coll Surg. Feb. 2010;210(2):205-9. (Abstract Only).
Kanai et al., (2009) The analgesic effect of a metered-dose 8% lidocaine pump spray in posttraumatic peripheral neuropathy: a pilot study. Anesth Analg. Mar. 2009;108(3):987-91. (Abstract Only).
Khaliq et al., (2007) Topical lidocaine for the treatment of postherpetic neuralgia. Cochrane Database Syst Rev. Apr. 18, 2007;(2):CD004846. (Abstract Only).
Tornblom-Paulander et al., (2015) Novel topical formulation of lidocaine provides significant pain relief for intrauterine device insertion: pharmacokinetic evaluation and randomized placebo-controlled trial. Fertil Steril. Feb. 2015;103(2):422-7.
Samarai et al., (2014) Pupil dilation with intra-cameral lidocaine versus topical midriatics during phacoemulsification. Glob J Health Sci. Sep. 18, 2014;6(7 Spec No):8-12.
Farrington et al., (2015) Pain management prior to nasogastric tube placement: atomized lidocaine. ORL Head Neck Nurs. 2015 Winter;33(1):8-16. (Abstract Only).
Cohen et al., (2014) Topical lidocaine gel with and without subconjunctival lidocaine injection for intravitreal injection: a within-patient study. Ophthalmic Surg Lasers Imaging Retina. Jul.-Aug. 2014;45(4):306-10.
Hizli et al., (2015) Novel approach for pain control in patients undergoing prostate biopsy: iliohypogastric nerve block with or without topical application of prilocaine-lidocaine: a randomized controlled trial. Urol J. Feb. 22, 2015;12(1):2014-9.
Shamra et al., (2015) Is Nebulized Lidocaine Adequate Topical Anesthesia for Diagnostic Transnasal Tracheoscopy? Ann Otol Rhinol Laryngol. Jul. 2015;124(7):545-9. (Abstract Only).
Kaur et al., (2015) A Randomized Trial of 1% vs 2% Lignocaine by the Spray-as-You-Go Technique for Topical Anesthesia During Flexible Bronchoscopy. Chest. Sep. 2015;148(3):739-45.
Zempsky et al., (1997) EMLA versus TAC for topical anesthesia of extremity wounds in children. Ann Emerg Med. Aug. 1997;30(2):163-6. (Abstract Only).
Claeys et al., (2011) Management of pain associated with debridement of leg ulcers: a randomized, multicentre, pilot study comparing nitrous oxide-oxygen mixture inhalation and lidocaïne-

(56) References Cited

OTHER PUBLICATIONS prilocaïne cream. J Eur Acad Dermatol Venereol. Feb. 2011;25(2):138-44. (Abstract Only).
Avramidis et al., (2000) Reduction in pain associated with open carpal tunnel decompression. J Hand Surg Br. Apr. 2000;25(2):147-9. (Abstract Only).
Khan et al., (2014) Efficacy of combination of 0.2% GTN and lignocaine ointments in wound healing and pain relief after Milligan Morgan hemorrhoidectomy—a comparison with lignocaine and 0.2% GTN ointments separately. Int J Surg. 2014;12(4):329-33.
Minassian et al, (2002) Randomized trial of lidocaine ointment versus placebo for the treatment of postpartum perineal pain. Obstet Gynecol. Dec. 2002;100(6):1239-43 (Abstract Only).
Singer et al., (2001) LET versus EMLA for pretreating lacerations: a randomized trial. Acad Emerg Med. Mar. 2001;8(3):223-30.
Lok et al., (1999) EMLA cream as a topical anesthetic for the repeated mechanical debridement of venous leg ulcers: a double-blind, placebo-controlled study. J Am Acad Dermatol. Feb. 1999;40(2 Pt 1):208-13. (Abstract Only).
Hansson et al.,(1993) Repeated treatment with lidocaine/prilocaine cream (EMLA) as a topical anaesthetic for the cleansing of venous leg ulcers. A controlled study. Acta Derm Venereol. Jun. 1993;73(3):231-3. (Abstract Only).
Mattsson et al., (1999) Digital image analysis of erythema development after experimental thermal injury to human skin: effect of postburn topical local anesthetics (EMLA). Anesth Analg. May 1999;88(5):1131-6. (Abstract Only).
Liang et al., (2011) Topical anesthetic EMLA for postoperative wound pain in stereotactic gamma knife radiosurgery: a perspective, randomized, placebo-controlled study. Minim Invasive Neurosurg. Apr. 2011;54(2):75-8.
Descroix et al., (2011) Efficacy of topical 1% lidocaine in the symptomatic treatment of pain associated with oral mucosal trauma or minor oral aphthous ulcer: a randomized, double-blind, placebo-controlled, parallel-group, single-dose study. J Orofac Pain. 2011 Fall;25(4):327-32. (Abstract Only).
Rosenthal et al., (2001) Using a topical anaesthetic cream to reduce pain during sharp debridement of chronic leg ulcers. J Wound Care. Jan. 2001;10(1):503-5. (Abstract Only).
Enander Malmros et al., (1990) Plasma concentrations and analgesic effect of EMLA (lidocaine/prilocaine) cream for the cleansing of leg ulcers. Acta Derm Venereal. 1990;70(3):227-30. (Abstract Only).
Cousins et al., (2013) The safety and efficacy of KAI-1678- an inhibitor of epsilon protein kinase C (εPKC)-versus lidocaine and placebo for the treatment of postherpetic neuralgia: a crossover study design. Pain Med. Apr. 2013;14(4):533-40.
Sabatowski et al., (2012) Safety and efficacy outcomes of long-term treatment up to 4 years with 5% lidocaine medicated plaster in patients with post-herpetic neuralgia. Curr Med Res Opin. Aug. 2012;28(8):1337-46.
Wasner et al., (2005) Postherpetic neuralgia: topical lidocaine is effective in nociceptor-deprived skin. J Neurol. Jun. 2005;252(6):677-86. (Abstract Only).
Campbell et al., Systemic absorption of topical lidocaine in normal volunteers, patients with post-herpetic neuralgia, and patients with acute herpes zoster. J Pharm Sci. May 2002;91(5):1343-50. (Abstract Only).
Tajti et al., Topical acetylsalicylic acid versus lidocaine for postherpetic neuralgia: results of a double-blind comparative clinical trial. Neurobiology (Bp) 1999;7(2):103-8. (Abstract Only).
Rowbotham et al., (1995) Topical lidocaine gel relieves postherpetic neuralgia. Ann Neurol. 37(2):246-253. (Abstract Only).
Label for Diflucan (Fluconazole Tablets), Distributed by Roerig, a Division of Pfizer, Mar. 2013 (35 pages).
Label (Package Insert) for Azithromycin, Distributed by SICOR Pharmaceuticals, Inc., Dec. 2016 (18 pages).
Label for Bactroban (mupirocin), Distributed by GlaxoSmithKline, Dec. 2015 (10 pages).
FDA Prescribing Information for Nystatin Powder, Distributed by Mayne Pharma, Summarized by www.drugs.com (5 pages).
PCCA, "New, Exclusive PCCA Base, XyliFos™: Boost the LoxaSperse™ Power in Nasal Nebulization and Decrease your Cost", Aug. 7, 2015 (2 pages).
Medinvent, LLC, "The NasoNeb Nasal Nebulizer," Nov. 15, 2013, document of 3 pages.
PCCA, Xyifos Trademark Application No. 86642712, May 27, 2015, document of 8 pages.
Lexington Podiatry, How to Make an Antifungal Foot Soak for Treatment of Foot Fungus, Feb. 27, 2011, document of 7 pages.
Roerig, "Diflucan-fluconazole tablet, Diflucan-fluconazole powder, for suspension," Pfizer, Mar. 2013, document of 61 pages.
Pfizer, "Fluconazole Injection, USP, in Intravia Plastic Container," Pfizer Injectables, Aug. 2010, document of 4 pages, https://www.pfizer.com/files/products/uspi_fluconazole.pdf.
PCCA, "LoxaSperse™, Powder Excipient Base for Use in Nebulization and Irrigation Compounds," 2013, document of 3 pages.
Muraki et al. (2009) Inhaled montelukast inhibits cysteinyl-leukotriene-induced bronchoconstriction in ovalbumin-sensitized guinea-pigs: the potential as a new asthma medication. Int Immunopharmacol. 9(11):1337-1341. (Abstract Only).
Nascimento et al. (2011) Topical betamethasone and hyaluronidase in the treatment of phimosis in boys: a double-blind, randomized, placebo-controlled trial. Int Braz J Urol. 37(3):314-319.
Nnichols et al. (2012) Safety and efficacy of topical azithromycin ophthalmic solution 1.0% in the treatment of contact lens-related dry eye. Eye Contact Lens. 38(2):73-79.
Nilfroushzadeh et al. (2009) Clindamycin lotion alone versus combination lotion of clindamycin phosphate plus tretinoin versus combination lotion of clindamycin phosphate plus salicylic acid in the topical treatment of mild to moderate acne vulgaris: a randomized control trial. Indian J Dermatol Venereol Leprol. 75(3):279-282.
O'Brien et al. (1995) Efficacy of ofloxacin vs cefazolin and tobramycin in the therapy for bacterial keratitis. Report from the Bacterial Keratitis Study Research Group. Arch Ophthalmol. 113(10):1257-1265. (Abstract Only).
Omidvari et al. (2007) Topical betamethasone for prevention of radiation dermatitis. Indian J Dermatol Venereol Leprol. 73(3):209. (Abstract Only).
Panahi et al. (2011) Doxepin cream vs betamethasone cream for treatment of chronic skin lesions due to sulfur mustard. Skinmed. 9(3):152-158. (Abstract Only).
Panda et al. (1996) Topical fluconazole therapy of Candida keratitis. Cornea. 15(4):373-375. (Abstract Only).
Pazoki-Toroudi et al. (2011) Combination of azelaic acid 5% and clindamycin 2% for the treatment of acne vulgaris. Cutan Ocul Toxicol. 30(4):286-291. (Abstract Only).
Philip et al. (2010) A phase I randomized, placebo-controlled, dose-exploration study of single-dose inhaled montelukast in patients with chronic asthma. J Asthma. 47(10):1078-1084. (Abstract Only).
Philip et al. (2011) The efficacy and tolerability of inhaled montelukast plus inhaled mometasone compared with mometasone alone in patients with chronic asthma. J Asthma. 48(5):495-502. (Abstract Only).
Pradeep et al. (2008) Clinical and microbiologic effects of subgingivally delivered 0.5% azithromycin in the treatment of chronic periodontitis. J Periodontol. 79(11):2125-2135. (Abstract Only).
Prevost et al. (2007) Palliative treatment of fingernail lichen planus. J Drugs Dermatol. 6(2):202-204. (Abstract Only).
Saraceno et al. (2014) Efficacy and maintenance strategies of two-compound formulation calcipotriol and betamethasone dipropionate gel (Xamiol® gel) in the treatment of scalp psoriasis: results from a study in 885 patients. J Dermatolog Treat. 25(1):30-33. (Abstract Only).
Scadding (2000) Other anti-inflammatory uses of intranasal corticosteroids in upper respiratory inflammatory diseases. Allergy. 55 Suppl 62:19-23.
Scheinfeld, (2008) Pruritic urticarial papules and plaques of pregnancy wholly abated with one week twice daily application of

(56) References Cited

OTHER PUBLICATIONS fluticasone propionate lotion: a case report and review of the literature. Dermatol Online J. 14(11):4.

Sharma et al. (2013) Comparative evaluation of topical versus intrastromal voriconazole as an adjunct to natamycin in recalcitrant fungal keratitis. Ophthalmology. 120(4):677-681.

Ship et al. (2007) Safety and effectiveness of topical dry mouth products containing olive oil, betaine, and xylitol in reducing xerostomia for polypharmacy-induced dry mouth. J Oral Rehabil. 34(10):724-732.

Sholapurkar et al. (2009) Comparison of efficacy of fluconazole mouthrinse and clotrimazole mouthpaint in the treatment of oral candidiasis. Aust Dent J. 54(4):341-346.

Silverman et al. (2003) Episodic viral wheeze in preschool children: effect of topical nasal corticosteroid prophylaxis. Thorax. 58(5):431-434.

Tai et al. (2013) Nasal carriage of *Staphylococcus aureus* in patients undergoing Mohs micrographic surgery is an important risk factor for postoperative surgical site infection: a prospective randomised study. Australas J Dermatol. 54(2):109-114. (Abstract Only).

Thorild et al. (2006) Caries in 4-year-old children after maternal chewing of gums containing combinations of xylitol, sorbitol, chlorhexidine and fluoride. Eur Arch Paediatr Dent. 7(4):241-245. (Abstract Only).

ULFF (2013) A potent steroid cream is superior to emollients in reducing acute radiation dermatitis in breast cancer patients treated with adjuvant radiotherapy. A randomised study of betamethasone versus two moisturizing creams. Radiother Oncol. 108(2):287-292. (Abstract Only).

Vander Salm et al. (1989) Reduction of sternal infection by application of topical vancomycin. J Thorac Cardiovasc Surg. 98(4):618-622. (Abstract Only).

Vural et al. (2003) The effect of topical fluticasone on nasal nitric oxide levels in a patient with allergic rhinitis. Ear Nose Throat J. 82(8):592-597. (Abstract Only).

Wu et al. (2013) An integrated analysis of the efficacy of fluticasone furoate nasal spray versus placebo on the nasal symptoms of perennial allergic rhinitis. Allergy Asthma Proc. 34(3):283-291. (Abstract Only).

Yactayo-Miranda et al. (2009) A prospective study determining the efficacy of topical 0.5% levofloxacin on bacterial flora of patients with chronic blepharoconjunctivitis. Graefes Arch Clin Exp Ophthalmol. 247(7):993-998.

Yim et al. (2010) Study to compare the efficacy and safety of fluconazole cream with flutrimazole cream in the treatment of superficial mycosis: a multicentre, randomised, double-blind, phase III trial. Mycoses. 53(6):522-529. (Abstract Only).

Yoon et al. (2007) Therapeutic effect of intracameral amphotericin B injection in the treatment of fungal keratitis. Cornea. 6(7):814-818. (Abstract Only).

FDA Prescribing Information for Clobetasol Ointment, Distributed by Taro Pharmaceuticals U.S.A., Inc., Apr. 2014, document of 8 pages.

FDA Prescribing Information for Fluocinonide Cream, Distributed by Taro Pharmaceuticals U.S.A., Inc., Aug. 2012, document of 7 pages.

FDA Prescribing Information for Econazole Nitrate Cream, Distributed by Taro Pharmaceuticals U.S.A., Inc., Sep. 2014, document of 4 pages.

PCCA, "Itraconazole 5%/Fluticasone Propionate 1% Spira-Wash™ Gel," PCCA Formula 10291, May 18, 2012, document of 3 pages.

Hong et al., (2014) Comparison of analgesic effect of preoperative topical diclofenac and ketorolac on postoperative pain after photorefractive keratectomy. J Cataract Refract Surg. 40(10):1689-1696.

Predel et al., (2012) Efficacy and safety of diclofenac diethylamine 2.32% gel in acute ankle sprain. Med Sci Sports Exerc. 44(9):1629-1636.

Barthel et al., (2009) Randomized controlled trial of diclofenac sodium gel in knee osteoarthritis. Semin Arthritis Rheum. 39(3):203-212.

Segatto et al., (2013) Comparative study of actinic keratosis treatment with 3% diclofenac sodium and 5% 5-fluorouracil. An Bras Dermatol. 88(5):732-738.

Akarsu et al., (2011) Comparison of topical 3% diclofenac sodium gel and 5% imiquimod cream for the treatment of actinic keratoses. Clin Exp Dermatol. 36(5):479-484.

\* cited by examiner

COMPOUNDED SOLUTIONS OF DICLOFENAC AND LIDOCAINE AND METHODS

FIELD OF THE INVENTION

The present application relates to compounded medications. In particular, the present application relates to compounded topical solutions and methods of making and using such compounded topical solutions.

BACKGROUND

Diclofenac sodium topical solution is a non-steroidal anti-inflammatory drug (NSAID) indicated for the treatment of signs and symptoms of osteoarthritis of the knee. For the relief of such signs and symptoms, the recommended dose of diclofenac sodium topical solution, 1.5% (w/w), is 40 drops on each painful knee, 4 times a day.

Lidocaine hydrochloride topical solution is a local anesthetic agent indicated for the production of topical anesthesia of accessible mucous membranes of the oral and nasal cavities and proximal portions of the digestive tract. When used as a spray, or when applied by cotton applicators or packs, as when instilled into a cavity, the suggested dosage of Lidocaine Hydrochloride Topical Solution, 4%, is 1 to 5 mL (40 to 200 mg lidocaine HCl), i.e., 0.6 to 3 mg/kg or 0.3 to 1.5 mg/lb body weight. When spraying, the solution is to be transferred from its original container to an atomizer.

SUMMARY

In one aspect, a compounded topical solution may include approximately 85% to approximately 95% (v/v) diclofenac sodium topical solution, 1.5% (w/w). The compounded topical solution may further include approximately 5% to approximately 15% (v/v) lidocaine hydrochloride topical solution, 4% USP.

In one example, the diclofenac sodium topical solution, 1.5% (w/w), is present in an amount between approximately 90% and approximately 93% (v/v) of the compounded topical solution and the lidocaine hydrochloride topical solution, 4% USP, is present in an amount between approximately 7% and approximately 10% (v/v) of the compounded topical solution.

In another example, the diclofenac sodium topical solution, 1.5% (w/w), is present in an amount approximately 90% (v/v) or more of the compounded topical solution and the lidocaine hydrochloride topical solution, 4% USP, is present in an amount approximately 7% (v/v) or more of the compounded topical solution.

In yet another example, the diclofenac sodium topical solution, 1.5% (w/w), is present in an amount approximately 91.7% (v/v) of the compounded topical solution and the lidocaine hydrochloride topical solution, 4% USP, is present in an amount approximately 8.32% (v/v) of the compounded topical solution.

In still yet another example, the compounded topical solution includes approximately 1.47% (w/v) diclofenac sodium and approximately 0.333% (w/v) lidocaine hydrochloride.

In another aspect, a method of making a compounded topical solution includes combining diclofenac sodium topical solution, 1.5% (w/w), and lidocaine hydrochloride topical solution, 4% USP. The method may further include mixing the combined diclofenac sodium topical solution, 1.5% (w/w), and lidocaine hydrochloride topical solution, 4% USP. The diclofenac sodium topical solution, 1.5% (w/w), may be combined in an amount between approximately 85% and approximately 95% (v/v) of the compounded topical solution and the lidocaine hydrochloride topical solution, 4% USP, may be combined in an amount between approximately 5% and approximately 15% (v/v) of the compounded topical solution.

In one example, the diclofenac sodium topical solution, 1.5% (w/w), is combined in an amount between approximately 90% and approximately 93% (v/v) of compounded topical solution and the lidocaine hydrochloride topical solution, 4% USP, is combined in an amount between approximately 7% and approximately 10% (v/v) of the compounded topical solution.

In another example, the diclofenac sodium topical solution, 1.5% (w/w), is combined in an amount approximately 90% (v/v) or more of the compounded topical solution and the lidocaine hydrochloride topical solution, 4% USP, is combined in an amount approximately 7% (v/v) or more of the compounded topical solution.

In yet another example, the diclofenac sodium topical solution, 1.5% (w/w), is combined in an amount approximately 91.7% (v/v) of the compounded topical solution and the lidocaine hydrochloride topical solution, 4% USP, is combined in an amount approximately 8.32% (v/v) of the compounded topical solution.

In still yet another example, the compounded topical solution includes approximately 1.47% (w/v) diclofenac sodium and approximately 0.333% (w/v) lidocaine hydrochloride.

The above-described and other features and advantages of the present disclosure will be appreciated and understood by those skilled in the art from the following detailed description, drawings, and appended claims.

DETAILED DESCRIPTION

Figure 1A:
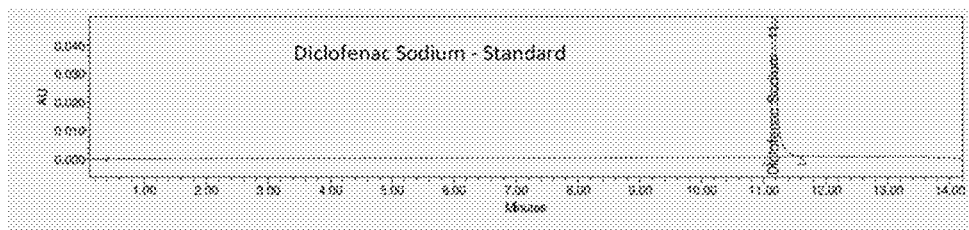
FIGS. 1A-1E are exemplary chromatograms of standard, untreated, heat treated, acid treated (45° C.), and acid treated (65° C.) Diclofenac Sodium samples, respectively, generated in a degradation study according to various embodiments described herein.

The present embodiments may relate to topically delivered or deliverable solutions of compounded medications for treatment of various ailments, such as inflammation or pain.

The compounded medications may typically include topical solutions that may be topically administered at a body surface. In one embodiment, a compounded topical solution for the effective administration of multiple medications simultaneously for treatment of one or more ailments may be provided. The compounded topical solution may include at least two active agents including a local anesthetic and a Non-Steroidal Anti-Inflammatory Drug (NSAID). The compounded topical solution may include all or some of the active agents in aqueous solution. In some embodiments, the topical solution comprises a compounded topical solution comprising at least two commercially available topical solutions that are compounded together. For example, a compounded topical solution may include a commercially available NSAID topical solution and a commercially available local anesthetic topical solution. In some embodiments, the compounded topical solution may further include multiple local anesthetics or NSAIDs obtained from commercially available solutions, commercially available creams, bulk powders, ground tablets, or combination thereof of such local anesthetics or NSAIDS.

In one embodiment, the compounded topical solution includes additional active agents selected from one or more anticonvulsants, nerve depressants, muscle relaxants, NMDA (N-Methyl-D-aspartate) receptor antagonists, opiate or opioid agonists, antidepressants, and/or other active agents.

The compounded topical solutions may be topically applied via any suitable mode of administration of the solution for the ailment treated, including, e.g., spray, drops, atomizer, wash, swab, sponge, absorbent dressing, instillation or irrigation. Ailments treated may include conditions such as inflammation, rheumatoid arthritis, osteoarthritis, lateral epicondylitis (tennis elbow), medial epicondylitis (golfer's elbow), chondromalacia patellae—CMP (runner's knee), tendonitis/carpel tunnel, soft tissue pain, fibromyalgia, diabetic neuropathy, peripheral neuropathy, neck pain, back pain, localized pain, plantar fasciitis, achilles tendonitis, tarsal tunnel—post-op massage, or heel pain. The compounded topical solution may exhibit excellent storage characteristics, and avoid separation and/or degradation of the active ingredients in the aqueous environment for substantial lengths of time.

As introduced above, the compounded topical solution may include a NSAID topical solution compounded with a local anesthetic topical solution. The NSAID component of the topical compounded solution may act to block the synthesis of prostaglandins by inhibiting cyclooxygenase-2 and cyclooxygenase-1, for example. In various embodiments, the NSAID may be selected from one or more salicylic acid derivatives (e.g., aspirin, diflunisal, salsalate, trilisate), one or more propionic acids (e.g., flurbiprofen, ibuprofen, ketoprofen, naproxen, oxaprozin), one or more acetic acids (e.g., diclofenac, etodolac, indomethacin, ketorolac, nabumetone, sulindac, tolmetin), one or more fenamates (e.g., meclofenamate), one or more oxicams (meloxicam, piroxicam), or one or more COX-2 inhibitors (e.g., celecoxib, rofecoxib, valdecoxib), or combinations thereof. For example, in one embodiment, the NSAID topical solution comprises a benzeneacetic acid derivative such as diclofenac or pharmaceutically acceptable salt thereof provided in an aqueous solution. In various embodiments, the local anesthetic may be selected from lidocaine, prilocaine, benzocaine, or combination thereof. The local anesthetic may be provided in an aqueous solution and compounded with the NSAID topical solution. One or both of the NSAID topical solution or the local anesthetic topical solution may be commercially available topical solutions. For example, the NSAID topical solution may include a commercially available diclofenac, or pharmaceutically acceptable salt thereof, topical solution and the local anesthetic topical solution may include a commercially available lidocaine, or pharmaceutically acceptable salt thereof, topical solution. In embodiments including one or more additional NSAIDs, local anesthetics, or both, the additional actives may be provided in commercially available solutions, creams, or pure powders or crushed commercial tablets and then combined with the compounded topical solution or a component thereof.

In various embodiments, the compounded topical solution may include a diclofenac topical solution comprising diclofenac in an aqueous solution. The diclofenac topical solution may be a commercially available diclofenac topical solution, such as diclofenac sodium solution for topical administration. The diclofenac sodium solution may contain, for example, 1.5% (w/w), diclofenac sodium wherein each 1 mL of solution contains approximately 16.05 mg of diclofenac sodium. In one embodiment, the diclofenac solution comprises a diclofenac sodium solution, 1.5% (w/w), such as that which is manufactured under the trade name PENNSAID® by Nuvo Manufacturing, Varennes, Quebec, Canada or Diclofenac Sodium Topical Solution, 1.5% (w/w), manufactured by Apotex Inc. Toronto, Ontario, Canada M9L 1T9 for Apotex Corp. Weston, Fla. 33326 for treating the pain of osteoarthritis of the knee. The diclofenac solution may also contain various inactive ingredients such as dimethyl sulfoxide USP (DMSO, 45.5% w/w), ethanol, glycerin, propylene glycol and purified water. In one embodiment, the diclofenac solution comprises a diclofenac sodium solution marketed under the trade name PENNSAID® and manufactured by Nuvo Manufacturing, Varennes, Quebec, Canada, in a 2% (w/w) diclofenac solution for treating the pain of osteoarthritis of the knee. Each gram of solution may contain approximately 20 mg of diclofenac sodium and various inactive ingredients such as dimethyl sulfoxide USP (DMSO, 45.5% w/w), ethanol, purified water, propylene glycol, and hydroxypropyl cellulose. In other embodiments, other concentrations of diclofenac solution, such as diclofenac sodium solutions, may be used.

In various embodiments, the compounded topical solution may include a lidocaine topical solution comprising lidocaine in an aqueous solution. The lidocaine topical solution may be a commercially available lidocaine topical solution, such as lidocaine hydrochloride solution for topical administration. The lidocaine hydrochloride solution may contain, for example, 4% lidocaine (w/v) wherein each mL includes 40 mg lidocaine HCl. For example, in one embodiment, the lidocaine topical solution may be Lidocaine Hydrochloride Topical Solution USP, 4% manufactured by IGI Labs, Inc., Buena, N.J., in 50 mL screw cap glass bottles. The lidocaine hydrochloride topical solution may contain various inactive ingredients such as methylparaben, purified water, and sodium hydroxide to adjust pH to 6.0-7.0.

The compounded topical solution formulated by combining a lidocaine hydrochloride topical solution and diclofenac sodium topical solution may include relatively low concentrations of the active ingredients compared to conventional topical formulations including one or more of the active ingredients. Due to the formulation and combination described herein, the present compounded topical solution may provide similar effectiveness while having an increased safety profile. The increased safety profile may be especially beneficial to patients with gastric bleeds, on blood thinners, etc. The compounded composition may also provide local anesthetics benefits while promoting deeper penetration into the skin and leveraging DMSO in the diclofenac sodium solution embedded into the compounded topical cream, e.g., 45.5% (w/w) of the diclofenac sodium solution compounded with the lidocaine hydrochloride solution.

In various embodiments, the compounded topical solution comprises diclofenac or diclofenac sodium at a concentration between 0.1% and 1.9% and lidocaine or lidocaine hydrochloride at a concentration of between 0.1% and 3.9%. In one example, the compounded topical solution includes approximately 0.5% or more, approximately 1.0% or more, or approximately 1.45% or more diclofenac or diclofenac sodium and approximately 0.2% or more, approximately 0.28% or more, or approximately 0.3% or more lidocaine or lidocaine hydrochloride. As used herein, the term approximately means+/−10% of the stated value it modifies. In some embodiments, the compounded topical solution includes between approximately 1.0% and approximately 1.9%, approximately 1.1% and approximately 1.8%, approximately 1.2% and approximately 1.7%, approximately 1.2% and approximately 1.6%, approximately 1.2% and approximately 1.5%, approximately 1.2% and approximately 1.4%, approximately 1.2% and approximately 1.3%, approximately 1.3% and approximately 1.6%, approximately 1.3% and approximately 1.5%, approximately 1.3% and approximately 1.4%, approximately 1.4% and approximately 1.6%, approximately 1.4% and approximately 1.5% (w/v) diclofenac or diclofenac sodium and between approximately 1.0%, approximately 0.2% and approximately 0.8%, approximately 0.2% and approximately 0.7%, approximately 0.2% and approximately 0.6%, approximately 0.2% and approximately 0.5%, approximately 0.2% and approximately 0.4%, approximately 0.2% and approximately 0.3%, approximately 0.3% and approximately 0.7%, approximately 0.3% and approximately 0.6%, approximately 0.3% and approximately 0.5%, approximately 0.3% and approximately 0.4%, approximately 0.330% and approximately 0.340% (w/v) lidocaine or lidocaine hydrochloride. For example, in various embodiments, the compounded topical solution comprises between approximately 1.0% and approximately 2.0%, such as between approximately 1.3% and approximately 1.6%, (w/v) diclofenac sodium and between approximately 0.1% and approximately 0.5%, such as between approximately 0.3% and approximately 0.35%, (w/v) lidocaine hydrochloride. In one embodiment, the compounded topical solution includes approximately 1.47% (w/v) diclofenac sodium and approximately 0.333% (w/v) lidocaine hydrochloride. In another embodiment, the compounded topical solution includes approximately 1.35% (w/v) diclofenac and approximately 0.4% (w/v) lidocaine. In various embodiments, a method of formulating the compounded topical solution includes combining a commercially available diclofenac sodium solution, diclofenac sodium topical solution, 1.5% (w/w), or diclofenac sodium topical solution 2.0% (w/w) solution, with a commercially available lidocaine solution, such as lidocaine hydrochloride topical solution, 4% USP, to form a compounded topical solution having one of the above listed concentrations (w/v) of diclofenac sodium and lidocaine hydrochloride. Stronger or weaker concentrations of diclofenac or diclofenac sodium topical solutions and lidocaine or lidocaine hydrochloride topical solutions may be used wherein the amounts of such solutions added are modified to achieve the appropriate w/v concentrations.

In various embodiments, the compounded topical solution comprises a commercially available diclofenac sodium topical solution, 1.5% (w/w), compounded with a commercially available lidocaine hydrochloride topical solution, 4% USP, wherein the compounded topical solution includes diclofenac sodium topical solution, 1.5% (w/w), at a concentration between 0.1% and 99%, such as between 50% and 95%, (v/v) and lidocaine hydrochloride topical solution, 4% USP, at a concentration between 0.1% and 90%, such as 0.2% and 5%, (v/v). In one example, the compounded topical solution includes approximately 80% or more, approximately 90% or more, or approximately 91.7% (v/v) diclofenac sodium topical solution, 1.5% (w/w), and approximately 4% or more, approximately 7% or more, or approximately 8.32% (v/v) lidocaine hydrochloride topical solution, 4% USP. In one embodiment, the compounded topical solution includes approximately 90% (v/v) diclofenac sodium topical solution, 1.5% (w/w), and approximately 10% (v/v) lidocaine hydrochloride topical solution, 4% USP. In some embodiments, the compounded topical solution includes between approximately 50% and approximately 98%, approximately 55% and approximately 97%, approximately 60% and approximately 96%, approximately 70% and approximately 95%, approximately 80% and approximately 95%, approximately 85% and approximately 95%, approximately 90% and approximately 95%, approximately 90% and approximately 94%, approximately 90% and approximately 93%, approximately 90% and approximately 92%, approximately 91% and approximately 93%, approximately 91% and approximately 92% (v/v) diclofenac sodium topical solution, 1.5% (w/w), and between approximately 2% and approximately 20%, approximately 4% and approximately 18%, approximately 6% and approximately 16%, approximately 6% and approximately 16%, approximately 6% and approximately 12%, approximately 6% and approximately 10%, approximately 7% and approximately 14%, approximately 7% and approximately 12%, approximately 7% and approximately 10%, approximately 8% and approximately 14%, approximately 8% and approximately 12%, approximately 8% and approximately 10% (v/v) lidocaine hydrochloride topical solution, 4% USP. For example, in various embodiments, the compounded topical solution comprises between approximately 80% and approximately 95%, such as between approximately 90% and approximately 93% (v/v) diclofenac sodium topical solution, 1.5% (w/w), and between approximately 4% and approximately 14%, such as between approximately 7% and approximately 10% (v/v) lidocaine hydrochloride topical solution, 4% USP. In one embodiment, the compounded topical solution includes approximately 91.7% diclofenac sodium and approximately 8.32% lidocaine hydrochloride topical solution, 4% USP. In various embodiments, a method of formulating the compounded topical solution includes combining a commercially available diclofenac sodium solution, such as diclofenac sodium topical solution, 1.5% (w/w), with a commercially available lidocaine solution, such as lidocaine hydrochloride topical solution, 4% USP, to form a compounded topical solution having one of the above listed concentrations (v/v) of diclofenac sodium topical solution, 1.5% (w/w), and lidocaine hydrochloride topical solution, 4% USP. Stronger or weaker concentrations of diclofenac or diclofenac sodium topical solutions and lidocaine or lidocaine hydrochloride topical solutions may be used wherein the amounts of such solutions added are modified to achieve the appropriate v/v concentrations.

As introduced above, a method of making a compounded topical solution may include combining, e.g., adding to each other, two commercially available topical solutions. The method may further include mixing the two combined solutions to form a compounding topical solution for administration of multiple active agents. Example 1 presents a method of making a compounded topical solution that includes approximately 1.47% diclofenac sodium (w/v) and approximately 0.333% (w/v) lidocaine hydrochloride. However, the method may be applied to make compounded topical solutions having other active concentrations, such as those described herein.

Example 1—Diclofenac Sodium/Lidocaine HCl Compounded Topical Solution 1.47/0.333%

Diclofenac sodium topical solution, 1.5% (w/w), and lidocaine hydrochloride topical solution, 4% USP, were compounded to make a compounded topical solution. Appropriate amounts of diclofenac sodium topical solution, 1.5% (w/w), and lidocaine hydrochloride topical solution, 4% USP, were measured. Diclofenac sodium topical solution, 1.5% (w/w), includes approximately 16.05 mg diclofenac sodium per mL. Accordingly, approximately 0.9167 mL of diclofenac sodium topical solution, 1.5% (w/w), was measured for every mL of compounded topical solution. Approximately 0.0832 mL of lidocaine hydrochloride topical solution, 4% USP, was measured for every mL of compounded topical solution. The measured ingredients where combined in a beaker. The beaker was placed on a magnetic stirring plate and a stir bar was placed in the beaker and rotated at a speed to create a small vortex for 5 minutes. The stirred solution was then placed in containers. Each mL of the compounded topical solution included approximately 91.7% (v/v) diclofenac sodium topical solution, 1.5% (w/w), and approximately 8.32% lidocaine hydrochloride topical solution, 4% USP.

Table I below depicts potency test results for the compounded topical solution of Example 1. Potency was determined via USP<621>HPLC, USP<851>Spectrophotometry, and specific monograph, using a High Performance Liquid Chromatography with an Ultraviolet/Photodiode Array Detector.

TABLE I

Potency Test

| Analyte | Reported | Measured | Test Potency | Test Method |
|---|---|---|---|---|
| Lidocaine Hydrochloride | 0.333% | 0.336% | 101% | HPLC with an Ultraviolet/ photodio de array |
| Diclofenac Sodium | 1.47 | 1.51% | 103% | HPLC |

In further embodiments, the method may also include combining one or more additional active agents comprising one or more additional NSAIDs selected from salicylic acid derivatives (e.g., aspirin, diflunisal, salsalate, trilisate), one or more propionic acids (e.g., flurbiprofen, ibuprofen, ketoprofen, naproxen, oxaprozin), one or more acetic acids (e.g., etodolac, indomethacin, ketorolac, nabumetone, sulindac, tolmetin), one or more fenamates (e.g., meclofenamate), one or more oxicams (meloxicam, piroxicam), or one or more COX-2 inhibitors (e.g., celecoxib, rofecoxib, valdecoxib), or combinations thereof, one or more additional local anesthetics selected from prilocaine, benzocaine, or combination thereof, one or more muscle relaxants selected from baclofen, carisoprodol, orphenadrine, cyclobenzaprine, dantrolene, tizanidine, amitriptyline, or combinations thereof, one or more NMDA receptor antagonists such as ketamine, or one or more opioid or opiate agonists selected from oxycodone, morphine, fentanyl, hydrocodone, codeine, butalbital, tramadol, or combinations thereof, one or more nerve depressants selected from gabapentin, topiramate, lamotrigine, or combinations thereof, and/or other active agents. The additional active agents may be provided in powder form (e.g., pure powder or crushed tablets), suspension, gel, solution, or cream, e.g., emulsion. The additional active agents may comprise 0.1% to 5% (w/v) of the compounded topical solution.

In further embodiments, the compounded topical solution may be further compounded with a cream to form a compounded transdermal cream for topical/transdermal administration. As used herein, cream is intended to include a cream, ointment, lotion, gel, emulsion (oil in water or water in oil), etc. unless stated otherwise. In some embodiments, the compounded topical solution is compounded with a commercially available cream, which may or may not include additional active agents.

The compounded topical solution or derivative thereof may be topically applied to a body surface utilizing for example, spray, drops, atomizer, wash, swab, sponge, absorbent dressing, instillation or irrigation. Topical application may be with respect to body surfaces such as trunk, limbs, hands, feet, neck, head, cavities, etc. In various embodiments, the compounded topical solution may find orthopedic application, e.g., as part of a therapeutic treatment of rheumatoid arthritis/osteoarthritis, lateral epicondylitis (tennis elbow), medial epicondylitis (golfer's elbow), chondromalacia patellae—CMP (runner's knee), or tendonitis/carpel tunnel; rheumatologic application, e.g., as part of a therapeutic treatment of soft tissue pain, fibromyalgia, diabetic neuropathy, peripheral neuropathy, rheumatoid arthritis, or osteoarthritis; neurologic application, e.g., as part of a therapeutic treatment diabetic neuropathy, peripheral neuropathy, fibromyalgia, or localized pain; podiatric application, e.g., as part of a therapeutic treatment of diabetic neuropathy, peripheral neuropathy, plantar fasciitis, Achilles tendonitis, tarsal tunnel—post-op massage, or heel pain—which may include usage in conjunction with urea; pain management application, e.g., as part of a therapeutic treatment of soft tissue pain, fibromyalgia, diabetic/peripheral neuropathy, rheumatoid arthritis, osteoarthritis, or neck and back pain; or ear nose and throat or dental applications, e.g., as part of a therapeutic treatment of temporomandibular joint disorder (TMJD or TMJ), or trigeminal neuralgia.

The present disclosure also includes a stability-indicating method for the analysis of compounded solutions. As presented in the following example forced degradation study performed on a compounded solution preparation comprising Diclofenac Sodium/Lidocaine HCl Solution 1.47%/0.333%, the methods used are stability-indicating. The methods described below and similar may be used to establish stability-indicating methods for analysis of other compounded solutions using similarly designed forced degradation studies.

At least two degradation conditions may be used to determine specificity. In the exemplary protocol, two degradation conditions, heat and acid, were used. With respect to the heat degradation condition, 1 gram samplings of the preparation were heated at 40° C., 65° C., and 80° C. At day 2, day 6, and day 8 the treated samples were taken out and analyzed. With respect to the acid degradation condition, 120 uL of 0.1N HCl was added to 1 gram samplings of the preparation. The acid degradation treated samplings were then either kept at room temperature or heated at 40° C. and 65° C. At day 2, day 6, and day 8, the treated samplings were taken out and analyzed. Acid degradation condition also included 0.333 mL of sample incubated with 0.333 mL of concentrated sulfuric acid at 40° C. and 65° C. These treated samples where then analyzed after 14 hours and 18 hours of incubation. The 0.333 mL samples were prepared for analysis by dilution to 50 mL with methanol. Samplings of the heat and acid treated preparations were treated the same way. Lidocaine standard was prepared by accurately weighing and dissolving Lidocaine Hydrochloride USP Monohydrate (PCCA, C169931) in Methanol to a final concentration of 100 µg/mL. Diclofenac standard was prepared by accurately weighing and dissolving Diclofenac Sodium USP (PCCA, C164795) in Methanol to a similar final concentration.

Standards and samples for were analyzed with a gradient method on a Waters Acquity UPLC equipped with a PDA detector. Eluent A was prepared by adding 1 mL of Trifluroacetic acid to 1 L of DI Water. Eluent B was prepared by adding 1 mL of Trifluoroacetic acid to 1 L of Acetonitrile. The flow rate was 1 mL per minute. The column temperature was 50° C. The injection volume was 2 uL. The sample tray was kept at 22° C. The LC column was Acclaim RSLC PA2 Polar Advantage II, 2.2 um 120 A 2.1×150 mm from Thermo Scientific. The analysis time was 14 minutes with an additional 1 minute delay. The gradient was set as described in Table II. The processing wavelengths were 225 nm for Lidocaine and 276 nm for Diclofenac Sodium.

TABLE II

Gradient Used for Analysis of Standards and Samples

| Minutes | Eluent A % | Fluent B % |
|---|---|---|
| 0 | 98.0 | 2.0 |
| 6 | 88.0 | 12.0 |
| 13 | 20.0 | 80.0 |
| 13.2 | 98.0 | 2.0 |

Figure 1B:
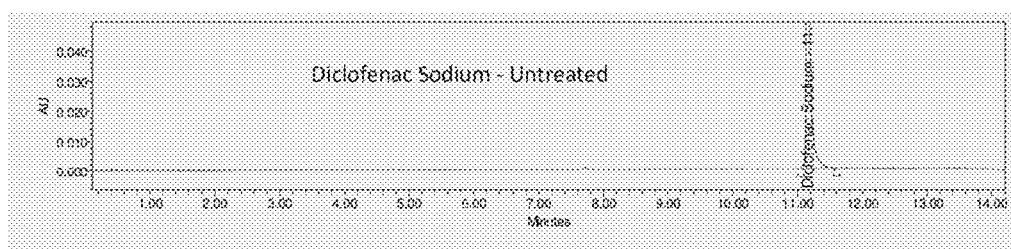
Figure 1C:
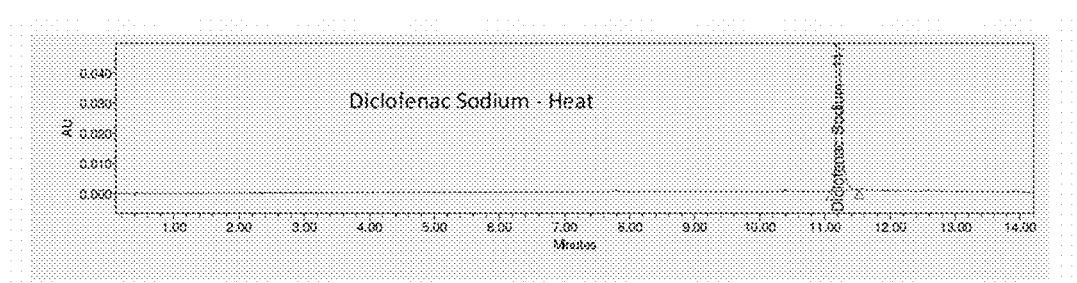
Figure 1D:
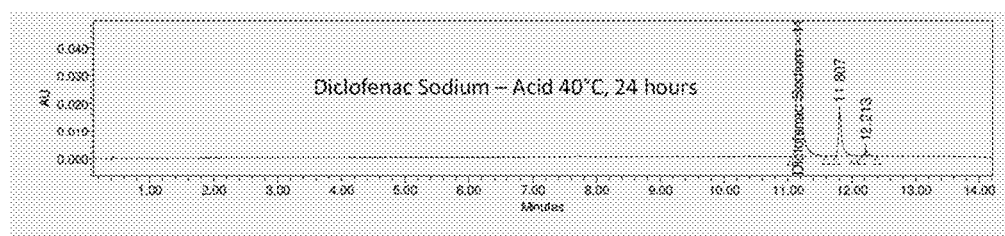
Figure 1E:
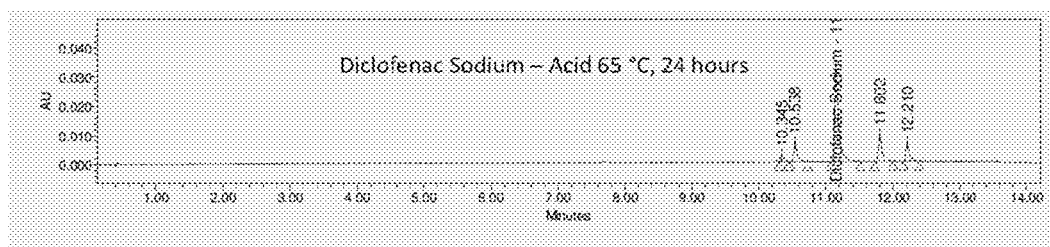

Percent recoveries of Diclofenac Sodium for untreated and treated samples are shown in Table III. FIGS. 1A-1E present exemplary chromatograms of standard, untreated, heat treated, acid treated at 45° C., and acid treated at 65° C. Diclofenac Sodium samples, respectively. Retention time for Diclofenac Sodium is at 11.5 minutes.

TABLE III

Recovery of Diclofenac Sodium (%)

|  | Day 0 | Day 2 | Day 6 | Day 8 |
|---|---|---|---|---|
| Untreated | 103 | 104 | 104 | 104 |
| 40° C. |  | 106 | 103 | 105 |
| 65° C. |  | 106 | 101 | 103 |
| 80° C. |  | 99.6 | 95.6 | 89.4 |
| H+, RT |  | 86.3 | 63.3 | 57.0 |
| H+, 40° C. |  | 70.8 | 44.5 | 28.0 |
| H+, 65° C. |  | 33.3 | 0.0 | 0.0 |

RT = 22-25° C.

Figure 2A:
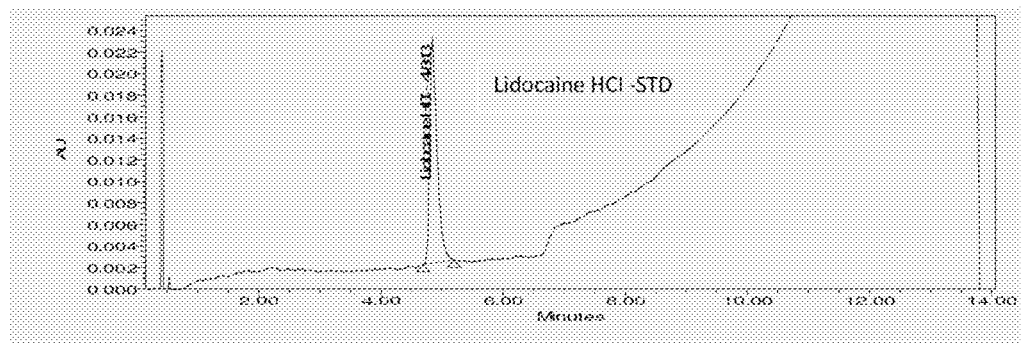
FIGS. 2A-2D are exemplary chromatograms of standard, untreated, heat treated, and acid treated Lidocaine HCl samples, respectively, generated in a degradation study according to various embodiments described herein.
Figure 2B:
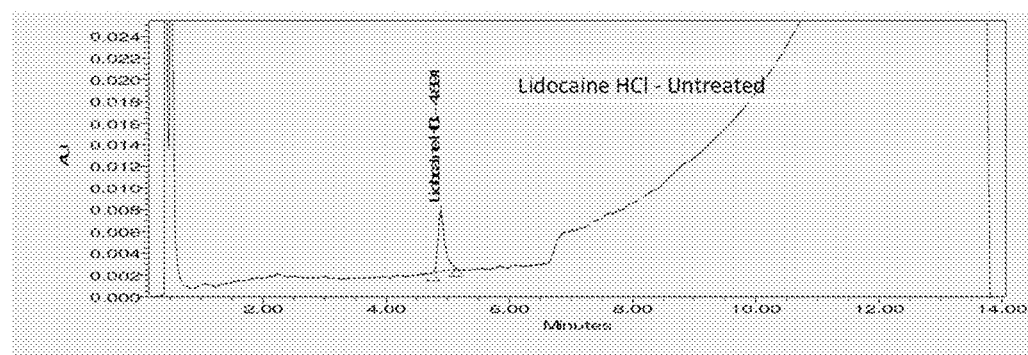
Figure 2C:
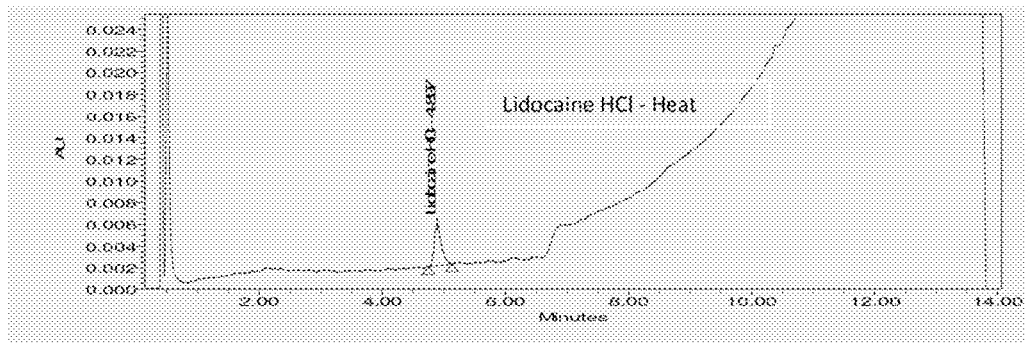
Figure 2D:
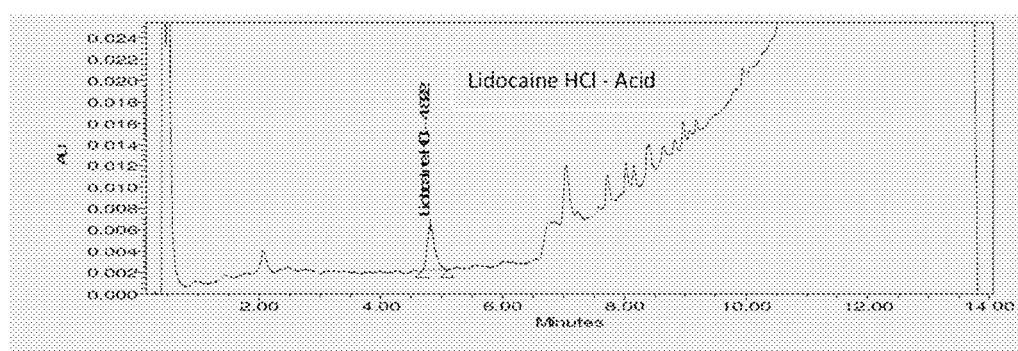

Percent recoveries of Lidocaine HCl for untreated and treated samples are shown in Table IV. FIGS. 2A-2D present exemplary chromatograms of standard, untreated, heat treated, and an acid treated Lidocaine HCl samples, respectively. Retention time for Lidocaine HCl is at 4.89 minutes.

TABLE IV

Recovery of Lidocaine HCl (%)

|  | Day 0 | Day 2 | Day 6 | Day 8 |
|---|---|---|---|---|
| Untreated | 101 | 101 | 102 | 104 |
| 40° C. |  | 100 | 99.4 | 104 |
| 65° C. |  | 108 | 94.5 | 97.5 |
| 80° C. |  | 96.0 | 99.9 | 75.6 |
| H+, RT |  | 98.5 | 96.5 | 101 |
| H+, 40° C. |  | 101 | 103 | 96.4 |
| H+, 65° C. |  | 97.0 | 102 | 101 |

RT = 22-25° C.

Percent recoveries of Lidocaine HCl for sulfuric acid treated samples are shown in Table V.

TABLE V

Recovery of Lidocaine HCl (%)

|  | 14 Hours | 18 Hours |
|---|---|---|
| Control | 102 | 102 |
| H2SO4, 40° C. | 96.3 | 75.4 |
| H2SO4, 65° C. | 86.2 | 73.9 |

The above degradation study performed for Diclofenac Sodium and Lidocaine HCl Solution in Diclofenac Sodium/Lidocaine HCl Solution 1.47%/0.333% shows no co-elution or interference between degradants and API in all samples (stressed and untreated), thus, it demonstrates specificity. The methods used for this study are therefore stability-indicating methods.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular preferred arrangements disclosed for carrying out this invention, but that the invention will include all embodiments and arrangements falling within the scope of the appended claims.

What is claimed is:

1. A method of making a compounded topical solution, the method comprising:
    combining a diclofenac sodium topical solution, 1.5% (w/w), and a lidocaine hydrochloride topical solution, 4% USP; and
    mixing the combined diclofenac sodium topical solution, 1.5% (w/w), and lidocaine hydrochloride topical solution, 4% USP;
    wherein the diclofenac sodium topical solution, 1.5% (w/w), comprises DMSO, 45.5% (w/w), and propylene glycol and is combined in an amount between approximately 85% and approximately 95% (v/v) of the compounded topical solution and the lidocaine hydrochloride topical solution, 4% USP, is combined in an amount between approximately 5% and approximately 15% (v/v) of the compounded topical solution.

2. The method of claim 1, wherein the diclofenac sodium topical solution, 1.5% (w/w), is combined in an amount between approximately 90% and approximately 93% (v/v) of compounded topical solution and the lidocaine hydrochloride topical solution, 4% USP, is combined in an amount between approximately 7% and approximately 10% (v/v) of the compounded topical solution.

3. The method of claim 1, wherein the diclofenac sodium topical solution, 1.5% (w/w), is combined in an amount approximately 90% (v/v) or more of the compounded topical solution and the lidocaine hydrochloride topical solution, 4% USP, is combined in an amount approximately 7% (v/v) or more of the compounded topical solution.

4. The method of claim 1, wherein the diclofenac sodium topical solution, 1.5% (w/w), is combined in an amount approximately 91.7% (v/v) of the compounded topical solution and the lidocaine hydrochloride topical solution, 4% USP, is combined in an amount approximately 8.32% (v/v) of the compounded topical solution.

5. The method of claim 1, wherein the compounded topical solution comprises approximately 1.47% (w/v) diclofenac sodium and approximately 0.333% (w/v) lidocaine hydrochloride.

6. The method of claim 1, wherein the diclofenac sodium topical solution, 1.5% (w/w), is combined in an amount between approximately 90% and approximately 93% (v/v) of compounded topical solution and the lidocaine hydrochloride topical solution, 4% USP, is combined in an amount between approximately 7% and approximately 10% (v/v) of the compounded topical solution.

7. The method of claim 6, wherein the compounded topical solution comprises approximately 1.47% (w/v) diclofenac sodium and approximately 0.333% (w/v) lidocaine hydrochloride.

\* \* \* \* \*